(12) United States Patent
Yamada et al.

(10) Patent No.: US 8,965,096 B2
(45) Date of Patent: Feb. 24, 2015

(54) RADIATION THERAPY DEVICE CONTROLLER, PROCESSING METHOD AND PROGRAM FOR SAME

(75) Inventors: Masahiro Yamada, Tokyo (JP); Yasunobu Suzuki, Tokyo (JP); Kunio Takahashi, Tokyo (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 45 days.

(21) Appl. No.: 13/993,944
(22) PCT Filed: Oct. 27, 2011
(86) PCT No.: PCT/JP2011/074772
§ 371 (c)(1),
(2), (4) Date: Jun. 13, 2013
(87) PCT Pub. No.: WO2012/127727
PCT Pub. Date: Sep. 27, 2012

(65) Prior Publication Data
US 2013/0266202 A1 Oct. 10, 2013

(30) Foreign Application Priority Data
Mar. 18, 2011 (JP) ................................. 2011-061021

(51) Int. Cl.
*G06K 9/00* (2006.01)
*G06T 11/00* (2006.01)
(Continued)

(52) U.S. Cl.
CPC ............... *G06T 11/003* (2013.01); *A61B 6/032* (2013.01); *A61B 6/5288* (2013.01); *A61B 6/541* (2013.01); *A61N 5/1049* (2013.01); *A61N 2005/1061* (2013.01)
USPC ................. 382/131; 600/425; 600/1; 378/62; 250/491.1

(58) Field of Classification Search
CPC ..................... G06T 11/003; A61N 2005/1061; A61N 5/1049; A61N 2005/1052; A61B 6/5288; A61B 6/541; A61B 6/032
USPC .......... 382/100, 128–134, 147; 600/425, 407, 600/427, 426.1; 378/62, 4, 10, 64–65, 197; 250/491.1; 315/500
See application file for complete search history.

(56) References Cited

U.S. PATENT DOCUMENTS 7,920,670 B2\* 4/2011 Hugg et al. ........................ 378/4
2006/0074292 A1 4/2006 Thomson et al.
(Continued)

FOREIGN PATENT DOCUMENTS

EP 2 662 115 A1 11/2013
JP 60-17568 A 1/1985
(Continued)

OTHER PUBLICATIONS

International Search Report, mailed Dec. 6, 2011, issued in PCT/JP2011/074772.
(Continued)

*Primary Examiner* — Shefali Goradia
(74) *Attorney, Agent, or Firm* — Birch, Stewart, Kolasch & Birch, LLP

(57) ABSTRACT

A radiation therapy device controller identifies a pixel on a straight line connecting a ray source and a sensor array, and calculates a luminance update amount candidate value for each identified pixel based on a ratio of a change amount for the pixel on the straight line indicating the living body to a sum of change amounts from a luminance value of a pixel corresponding to a correlated computed tomography image correlated with a computed tomography image of an update target of a luminance value of the identified pixel. Also, the control device calculates a luminance update amount of each identified pixel using the luminance update amount candidate value of each identified pixel calculated for a plurality of rotation angles, and updates the luminance value of each corresponding pixel of the computed tomography image of the update target using the luminance update amount of each identified pixel.

7 Claims, 7 Drawing Sheets

(51) Int. Cl.
*A61B 6/03* (2006.01)
*A61B 6/00* (2006.01)
*A61N 5/10* (2006.01)

(56) References Cited

U.S. PATENT DOCUMENTS

2008/0063250 A1  3/2008  Ozawa
2010/0119032 A1  5/2010  Yan et al.
2010/0158341 A1* 6/2010  Baumgart .................... 382/132

FOREIGN PATENT DOCUMENTS

| JP | 3708434 B2 | 10/2005 |
|---|---|---|
| JP | 2006-51199 A | 2/2006 |
| JP | 2007-503926 A | 3/2007 |
| JP | 2008-514352 A | 5/2008 |
| JP | 4126318 B2 | 7/2008 |
| JP | 2009-507524 A | 2/2009 |
| JP | 2010-500151 A | 1/2010 |
| JP | 2010-69086 A | 4/2010 |
| JP | 2012-196260 A | 10/2012 |
| WO | WO 2012/127724 A | 9/2012 |

OTHER PUBLICATIONS

Written Opinion of the International Searching Authority, mailed Dec. 6, 2011, issued in PCT/JP2011/074772.
European Search Report mailed Aug. 12, 2014 for related Application No. 11861548.3.

* cited by examiner

RADIATION THERAPY DEVICE CONTROLLER, PROCESSING METHOD AND PROGRAM FOR SAME

TECHNICAL FIELD

The present invention relates to a radiation therapy device controller that generates a CT image based on radiation radiated to a living body and tracks a position of a diseased portion in the living body, and a processing method and program for the same. Priority is claimed on Japanese Patent Application No. 2011-061021, filed Mar. 18, 2011, the content of which is incorporated herein by reference.

BACKGROUND ART

A radiation therapy device controller identifies a position in a living body to be irradiated with radiation based on a position of a diseased portion (tumor) displayed on a CT image (a computed tomography image) and irradiates the position with radiation.

The diseased portion, such as a tumor in the living body, varies under the influence of respiration or the like. Therefore, it is necessary to identify a diseased portion whose position varies in each of CT images that are generated sequentially over time and identify the position to be irradiated with radiation based on the position of the diseased portion.

Here, in order to improve identification accuracy of the position to be irradiated with radiation, it is necessary to accurately identify the diseased portion within the living body using the CT image. If the image quality of the CT image is improved, it is possible to accurately identify the position of the diseased portion and accurately identify the position to be irradiated with radiation by tracking the identified diseased portion. Methods of generating a CT image include an FBP method (Filtered Back Projection method).

The FBP method is an algorithm used to generate a general CT image, and is technology of reversely projecting X-ray projection data through a fast Fourier transform to perform image reconstruction. However, although there is an advantage in that a computation time for generation of the CT image using the FBP method is short, deterioration of image quality such as generation of artifacts in the image becomes a problem particularly if the amount of projection data used for reconstruction is small. Here, CT image generation technology for resolving a problem of degradation of image quality includes a successive approximation method (an Iterative Reconstruction method). Patent Documents 1 and 2 disclose the technology of the Iterative Reconstruction method.

PRIOR ART DOCUMENT

Patent Document

Patent Document 1: Japanese Patent No. 3708434
Patent Document 2: Japanese Unexamined Patent Application, First Publication No. S60-17568

SUMMARY OF INVENTION

Problem to be Solved by the Invention

In the technology of the successive approximation method described above, a virtual projection image is generated by projecting a CT image in the same direction as a radiation projection image, and an error is calculated between the virtual projection image and the radiation projection image generated by radiating radiation in the same direction as a projection direction of the virtual projection image. Also, the technology of the Iterative Reconstruction method is technology that reflects the error in the CT image and performs calculation of repetition of the generation of the virtual projection image and the calculation of the error between the virtual projection image and the radiation projection image to minimize the error, to thereby generate a CT image in which the error is small. However, although image quality of the CT image generated using the technology of the Iterative Reconstruction method is improved as compared to that of a CT image generated using an FBP method, in order to minimize the error between the radiation projection image and the virtual projection image for all pixel errors, a process of reflecting the error on the CT image is performed repeatedly. Accordingly, there is a problem in that generating the CT image using the Iterative Reconstruction method increases calculation time.

An object of the present invention is to provide a radiation therapy device controller, and a processing method and program for the same that are capable of solving the problems described above.

Means for Solving the Problem

A first aspect of the present invention is a radiation therapy device controller for controlling a radiation therapy device that irradiates a living body arranged between a ray source and a sensor array with radiation from the ray source to treat a diseased portion of the living body, the controller including a CT image selection unit that selects, as CT image data of an update target, CT image data of a set body motion phase from a CT image data group generated for each body motion phase in advance. The CT image is generated based on information detected by the sensor array, The radiation therapy device controller may include: a radiation projection image generation unit that rotates the ray source and the sensor array to generate a radiation projection image corresponding to each of a plurality of rotation angles, and records the radiation projection image, the rotation angle when rotating the ray source and the sensor array at the time of generating the radiation projection image, and a body motion phase at the time of generating the radiation projection image to be correlated with each other; a rotation angle detection unit that detects the rotation angle at the time of generating the radiation projection image; a reconstructed image generation unit that generates a reconstructed image when the CT image data of the update target is projected from the ray source to the sensor array at the detected rotation angle; a difference information generation unit that compares each pixel of the radiation projection image with each pixel of the generated reconstructed image to generate difference information indicating a luminance difference for the each pixels; a luminance update amount calculation unit that identifies a pixel on a straight line connecting the ray source and a detection element of the sensor array in the CT image data of the update target, calculates a luminance update amount candidate value for each identified pixel based on a degree of easiness of change in the luminance value of the identified pixel and the difference information, and calculates a luminance update amount of each identified pixel using the luminance update amount candidate value of each identified pixel calculated for a plurality of rotation angles corresponding to the body motion phase that is a target; and an updating unit that updates a luminance value of each corresponding pixel of the CT image data of the update target, using the luminance update amount of each identified pixel.

The initially set CT image and an image of a range in which the updating unit performs updating may be a CT image in a range wider than a range of a CT image generated based on radiation projection images of a plurality of rotation angles.

Further, according to a second aspect of the present invention, the luminance update amount calculation unit obtains the degree of easiness of change in the luminance value based on a difference between an initially set CT image of a body motion phase close to the body motion phase of the CT image data of the update target and an initially set CT image of another body motion phase close to the body motion phase of the initially set CT image.

Further, according to a third aspect of the present invention, the luminance update amount calculation unit obtains the degree of easiness of change in the luminance value based on a difference between an initially set CT image of a body motion phase close to the body motion phase of the CT image data of the update target and the CT image data of the update target generated based on the radiation projection image corresponding to an arbitrary body motion phase.

Further, according to the third aspect of the present invention, the radiation therapy device controller may include a diseased portion position tracking unit that calculates a position of the diseased portion corresponding to a measured body motion phase of the living body to track the diseased portion position using a correlation model formula showing a correlation between the body motion phase of the living body and the position of the diseased portion in the living body.

Further, a fourth aspect of the present invention is a processing method for a radiation therapy device controller for controlling a radiation therapy device that irradiates a living body arranged between a ray source and a sensor array with radiation from the ray source to treat a diseased portion of the living body, and generating a computed tomography image (CT image) based on information detected by the sensor array. In the processing method, CT image data of a set body motion phase is selected, as CT image data of an update target, from a CT image data group generated for each body motion phase in advance, and the ray source and the sensor array are rotated to generate a radiation projection image corresponding to each of a plurality of rotation angles. Further, in the processing method, the rotation angle is correlated with a separately acquired respiratory phase, the rotation angle at the time of generating the radiation projection image is detected, and a reconstructed image when the CT image data of the update target is projected from the ray source to the sensor array at the detected rotation angle is generated. Further, in the processing method, each pixel of the identified radiation projection image is compared with each pixel of the generated reconstructed image to generate difference information indicating a luminance difference for the pixels, and a pixel on a straight line connecting the ray source and the sensor array is identified in the CT image data of the update target. A luminance update amount candidate value is calculated for each identified pixel based on a degree of easiness of change in the luminance value of the identified pixel and the difference information. Also, a luminance update amount of each identified pixel is calculated using the luminance update amount candidate value of each identified pixel calculated for a plurality of rotation angles corresponding to the body motion phase that is a target. A luminance value of each corresponding pixel of the CT image data of the update target is updated using the luminance update amount of each identified pixel.

Further, a fifth aspect of the present invention is a program that controls a radiation therapy device that irradiates a living body arranged between a ray source and a sensor array with radiation from the ray source to treat a diseased portion of the living body. This program causes a computer of a radiation therapy device controller for generating a computed tomography image (CT image) based on information detected by the sensor array to function as: a CT image selection device that selects, as CT image data of an update target, CT image data of a set body motion phase from a CT image data group generated for each body motion phase in advance; a radiation projection image generation device that rotates the ray source and the sensor array to generate a radiation projection image corresponding to each of a plurality of rotation angles, and correlates the rotation angle with a separately acquired respiratory phase; a rotation angle detection device that detects the rotation angle at the time of generating the radiation projection image; and a reconstructed image generation device that generates a reconstructed image when the CT image data of the update target is projected from the ray source to the sensor array at the detected rotation angle. Further, this program causes the computer to function as: a difference information generation device that compares each pixel of the radiation projection image with each pixel of the generated reconstructed image to generate difference information indicating a luminance difference for the pixels; a luminance update amount calculation device that identifies, in the CT image data of the update target, a pixel on a straight line connecting the ray source and the sensor array, calculates a luminance update amount candidate value for each identified pixel based on a degree of easiness of change in the luminance value of the identified pixel and the difference information, and calculates a luminance update amount of each identified pixel using the luminance update amount candidate value of each identified pixel calculated for a plurality of rotation angles corresponding to the body motion phase that is a target; and an updating device that updates a luminance value of each corresponding pixel of the CT image data of the update target, using the luminance update amount of each identified pixel.

Effect of the Invention

According to the present invention, since the process of updating the data using the CT image data group (the initially set CT image data group) created in advance and recorded in the database is performed, it is possible to obtain a high-quality CT image in a short time by performing only the updating process using the newly generated radiation projection image.

Further, the luminance update amount is calculated only for each pixel whose luminance update amount candidate value has been calculated, the process of updating the CT image using the luminance update amount is performed, and the updating process is not performed on a pixel whose luminance update amount candidate value has not been calculated. Accordingly, it is possible to shorten a time to complete the updating process.

DESCRIPTION OF EMBODIMENTS

Hereinafter, a radiation therapy device controller, and a radiation therapy device controlled by the radiation therapy device controller according to an embodiment of the present invention will be described.

An embodiment of the present invention is assumed to create a CT image for each body motion phase of a periodic body motion such as respiration or heartbeat. However, a description in which only a respiratory phase is a target of the body motion will be given hereinafter for simplification.

In the present embodiment, a method of generating an initially set CT image data group generated for each respiratory phase in advance and a reconstructed CT image data group for each respiratory phase based on a radiation projection image generated at a time point at which a CT image is to be generated is shown.

Figure 1:
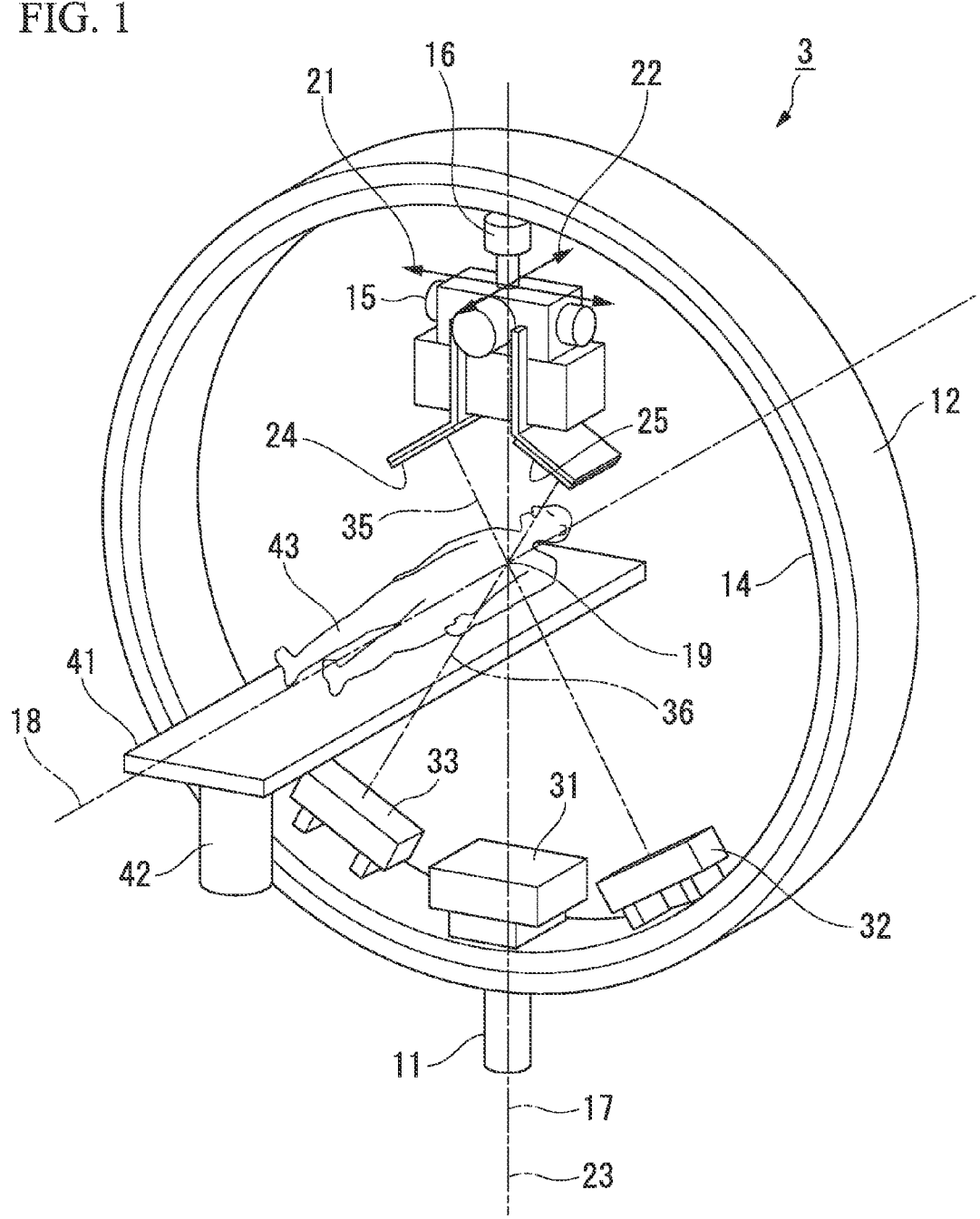
FIG. 1 is a diagram illustrating a configuration of a radiation therapy device.

First, an overview of the radiation therapy device that is a control target will be described. FIG. 1 shows a radiation therapy device.

As shown in FIG. 1, a radiation therapy device 3 includes a swivel driving device 11, an O ring 12, a traveling gantry 14, a head swing mechanism 15, and a therapeutic radiation radiating device 16. The swivel driving device 11 supports the O ring 12 against a base to be rotatable around a rotation axis 17, and rotates the O ring 12 around the rotation axis 17 under control of the radiation therapy device controller 1. The rotation axis 17 is parallel to a vertical direction. The O ring 12 is formed in a ring shape around a rotation axis 18 and supports the traveling gantry 14 to be rotatable around the rotation axis 18. The rotation axis 18 is perpendicular to the vertical direction and passes through an isocenter 19 included in the rotation axis 17. Further, the rotation axis 18 is fixed with respect to the O ring 12. That is, the rotation axis 18 is rotated around the rotation axis 17 together with the O ring 12. The traveling gantry 14 is formed in a ring shape around the rotation axis 18, and arranged to be concentric with the ring of the O ring 12. Further, the radiation therapy device 3 includes a traveling driving device, which is not shown. The traveling driving device rotates the traveling gantry 14 around the rotation axis 18 under control of the radiation therapy device controller 1.

The therapeutic radiation radiating device 16 is arranged at an inward side of the traveling gantry 14. The therapeutic radiation radiating device 16 radiates therapeutic radiation 23 under control of the radiation therapy device controller 1.

The head swing mechanism 15 is fixed to an inward side of the ring of the traveling gantry 14 and supports therapeutic radiation radiating device 16 against the traveling gantry 14. The head swing mechanism 15 has a pan axis 21 and a tilt axis 22. The pan axis 21 is fixed to the traveling gantry 14 and is parallel to the rotation axis 18 without intersecting the rotation axis 18. The tilt axis 22 is fixed to the traveling gantry 14 and orthogonal to the pan axis 21. The head swing mechanism 15 rotates the therapeutic radiation radiating device 16 around the pan axis 21 and rotates the therapeutic radiation radiating device 16 around the tilt axis 22 under control of the radiation therapy device controller 1.

As the therapeutic radiation radiating device 16 is supported by the traveling gantry 14 as described above, the therapeutic radiation 23 always substantially passes through the isocenter 19 even when the O ring 12 is rotated by the swivel driving device 11 and the traveling gantry 14 is rotated by the traveling driving device if the therapeutic radiation radiating device 16 is first adjusted to be directed to the isocenter 19 by the head swing mechanism 15. That is, the therapeutic radiation 23 can be radiated from an arbitrary direction to the isocenter 19 by performing the traveling and the swivel. Further, since the therapeutic radiation radiating device 16 or the like is a heavy object, there are cases in which the O ring itself is mechanically deformed according to traveling and the swivel. Also, there are cases in which the diseased portion does not necessarily match the isocenter. In this case, the therapeutic radiation radiating device 16 may be adjusted to be directed to the isocenter 19 or the diseased portion by the head swing mechanism 15 again, subsequent to setting of the traveling and the swivel.

Further, the radiation therapy device 3 includes a plurality of imager systems. That is, the radiation therapy device 3 includes diagnostic X-ray sources 24 and 25 and sensor arrays 32 and 33.

The diagnostic X-ray source 24 is supported by the traveling gantry 14. The diagnostic X-ray source 24 is arranged at the inward side of the ring of the traveling gantry 14 and arranged in such a position that an angle formed by a line segment connecting the isocenter 19 and the diagnostic X-ray source 24 and a line segment connecting the isocenter 19 and the therapeutic radiation radiating device 16 is an acute angle. The diagnostic X-ray source 24 radiates a diagnostic X-ray 35 toward the isocenter 19 under control of the radiation therapy device controller 1. The diagnostic X-ray 35 is a cone-beam in a cone shape radiated from one point of the diagnostic X-ray source 24 and having the point as a vertex. The diagnostic X-ray source 25 is supported by the traveling gantry 14. The diagnostic X-ray source 25 is arranged at the inward side of the ring of the traveling gantry 14 and arranged in such a position that an angle formed by a line segment connecting the isocenter 19 and the diagnostic X-ray source 25 and a line segment connecting the isocenter 19 and the therapeutic radiation radiating device 16 is an acute angle. The diagnostic X-ray source 25 radiates a diagnostic X-ray 36 toward the isocenter 19 under control of the radiation therapy device controller 1. The diagnostic X-ray 36 is a cone-beam in a cone shape radiated from one point of the diagnostic X-ray source 25 and having the point as a vertex.

The sensor array 32 is supported by the traveling gantry 14. The sensor array 32 receives the diagnostic X-ray 35 that is radiated by the diagnostic X-ray source 24 and then transmitted through a subject around the isocenter 19, and generates a radiation projection image of the subject. The sensor array 33 is supported by the traveling gantry 14. The sensor array 33 receives the diagnostic X-ray 36 that is radiated by the diagnostic X-ray source 25 and then transmitted through the subject around the isocenter 19, and generates a radiation projection image of the subject. An FPD (Flat Panel Detector) or an X ray II (Image Intensifier) is exemplified as the sensor arrays 32 and 33.

According to such imager systems, it is possible to generate the radiation projection image centered on the isocenter 19 based on image signals obtained by the sensor arrays 32 and 33.

The radiation therapy device 3 further includes a sensor array 31. The sensor array 31 is arranged in such a manner that a line segment connecting the sensor array 31 and the therapeutic radiation radiating device 16 passes through the isocenter 19 and is fixed to the inward side of the ring of the traveling gantry 14. The sensor array 31 receives the therapeutic radiation 23 that is radiated by the therapeutic radiation radiating device 16 and transmitted through the subject around the isocenter 19, and generates a radiation projection image of the subject. An FPD (Flat Panel Detector) or an X ray II (Image Intensifier) is exemplified as the sensor array 31.

When the traveling gantry 14 is caused to travel along the O ring 12, positional relationships between the diagnostic X-ray source 24 and the sensor array 32, the diagnostic X-ray source 25 and the sensor array 33, and the therapeutic radiation radiating device 16 and the sensor array 31 can be maintained during rotation around the rotation axis 18 passing through the isocenter 19. A rotation angle around the rotation axis 18 of the traveling gantry 14, the diagnostic X-ray sources 24 and 25, the therapeutic radiation radiating device 16 and the sensor arrays 31 to 33 relative to a predetermined position is hereinafter referred to simply as a rotation angle.

Further, the radiation therapy device 3 includes a treatment table 41 and a treatment table driving device 42. The treatment table 41 is used for a patient 43, which is treated, to lie on. The treatment table 41 includes a fastener, which is not shown. This fastener secures the patient to the treatment table 41 so that the patient does not move. The treatment table driving device 42 supports the treatment table 41 against a base and moves the treatment table 41 under control of the radiation therapy device controller 1.

Further, the radiation therapy device 3 includes an infrared camera, which is not shown, and detects a motion of an infrared marker attached to the living body using the infrared camera. The infrared marker performs a periodic motion in a period and a phase corresponding to a respiratory period and phase in the living body. When the radiation therapy device 3 irradiates the living body with radiation under the control of the radiation therapy device controller 1, the radiation therapy device 3 extracts the phase in the periodic motion of the infrared marker from the detected motion of the infrared marker, and notifies the radiation therapy device controller 1 of data of the extracted phase as information relating to the respiratory phase. Also, the radiation therapy device controller 1 generates CT image data based on the radiation projection image according to the initially set CT image data group, the different respiratory phases, and the plurality of rotation angles.

Figure 2:
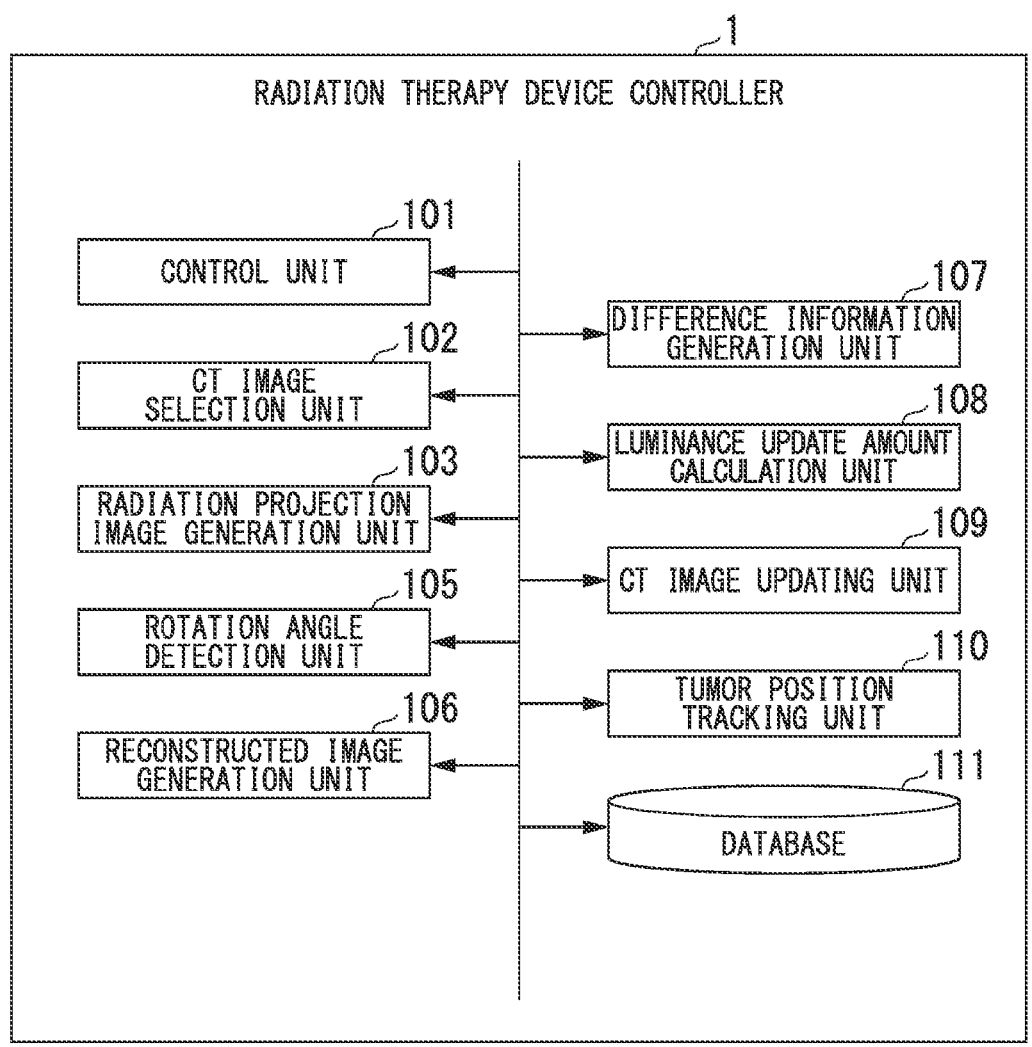
FIG. 2 is a block diagram illustrating a configuration of a radiation therapy device controller.

FIG. 2 is a block diagram illustrating a configuration of the radiation therapy device controller according to the same embodiment.

In FIG. 2, reference numeral 1 indicates the radiation therapy device controller that controls the radiation therapy device 3, which irradiates a living body arranged between a ray source and a sensor array arranged in a position facing the ray source with radiation along an irradiation axis from the ray source to treat a diseased portion of the living body. Here, the ray source refers to a diagnostic X-ray source or a therapeutic radiation radiating device. As shown in FIG. 2, the radiation therapy device controller 1 includes processing units of a CT image selection unit 102, a radiation projection image generation unit 103, a rotation angle detection unit 105, a reconstructed image generation unit 106, a difference information generation unit 107, a luminance update amount calculation unit 108, a CT image updating unit 109, and a diseased portion position tracking unit 110, a control unit 101 that controls each processing unit, and a database 111 that stores information used for processing in each processing unit.

An initially set CT image data group generated by radiating radiation to a living body of a person or the like that is subjected to radiation treatment has been stored in the database 111 in advance. The initially set CT image data group is a set of initially set CT image data of successive cross sections of the living body generated in advance for each respiratory phase of the living body. Further, the initially set CT image data group may be data generated by another device in advance or may be data generated by the radiation therapy device controller 1 in advance.

The CT image selection unit 102 is a processing unit that selects the initially set CT image data of a set respiratory phase from the initially set CT image data group.

The radiation projection image generation unit 103 is a processing unit that generates a radiation projection image corresponding to each of a plurality of rotation angles and correlates the rotation angle indicated by the generated radiation projection image with a separately acquired respiratory phase.

The rotation angle detection unit 105 is a processing unit that detects a rotation angle at the time of generation of an identified radiation projection image.

The reconstructed image generation unit 106 is a processing unit that generates a reconstructed image that is estimated to be obtainable from the sensor array (see FIG. 1) facing the ray source based on the initially set CT image data or reconstructed. CT image data in which a luminance value of a pixel in the initially set CT image data has been updated at each rotation angle.

Hereinafter, the radiation projection image is assumed to be a radiation projection image generated by the radiation radiated toward the sensor array 32 by the diagnostic X-ray source 24. Further, the embodiment of the present invention is similarly satisfied even when another ray source and another sensor array that face each other are used or when a plurality of sets of ray sources and sensor arrays that face each other are used.

The difference information generation unit 107 is a processing unit that compares each pixel of the identified radiation projection image with each pixel of the generated reconstructed image to generate difference information indicating a luminance difference between the pixels.

The luminance update amount calculation unit 108 is a processing unit that identifies, in the reconstructed CT image data, a pixel on a straight line connecting the diagnostic X-ray source 24 and the detection element of the sensor array 32 and calculates a luminance update amount of each identified pixel.

Further, the CT image updating unit 109 is a processing unit that updates the luminance value of each corresponding pixel of the reconstructed CT image data using the luminance update amount of each identified pixel.

Here, the radiation therapy device controller 1 compares the reconstructed CT image data after the update of the luminance value of each corresponding pixel of the reconstructed CT image data using the luminance update amount for each pixel with the reconstructed CT image data before the update of the luminance value of each corresponding pixel of the reconstructed CT image data. Also, when the luminance difference between the CT images is greater than or equal to a predetermined threshold value, the radiation therapy device controller 1 repeats processes of the reconstructed image generation unit 106, the difference information generation unit 107, the luminance update amount calculation unit 108, and the CT image updating unit 109 using the reconstructed CT image after the update. The threshold value is set in consideration of a statistical variation range of the luminance value.

Further, the diseased portion position tracking unit 110 is a processing unit that calculates a movement position of the measured diseased portion corresponding to the respiratory phase of the living body using a correlation model formula showing a correlation between the respiratory phase of the living body and a movement position of the diseased portion calculated in the reconstructed CT image data, and tracks the position of the diseased portion. There is a polynomial model formula, a non-parametric model formula or the like as a correlation model formula.

Next, a process flow of the radiation therapy device controller 1 that controls the radiation therapy device 3 will be described step by step.

Coordinates of the initially set CT image data and the reconstructed CT image data are aligned based on a position of a spine or the like that rarely moves in a body motion prior to the present process flow.

Figure 3:
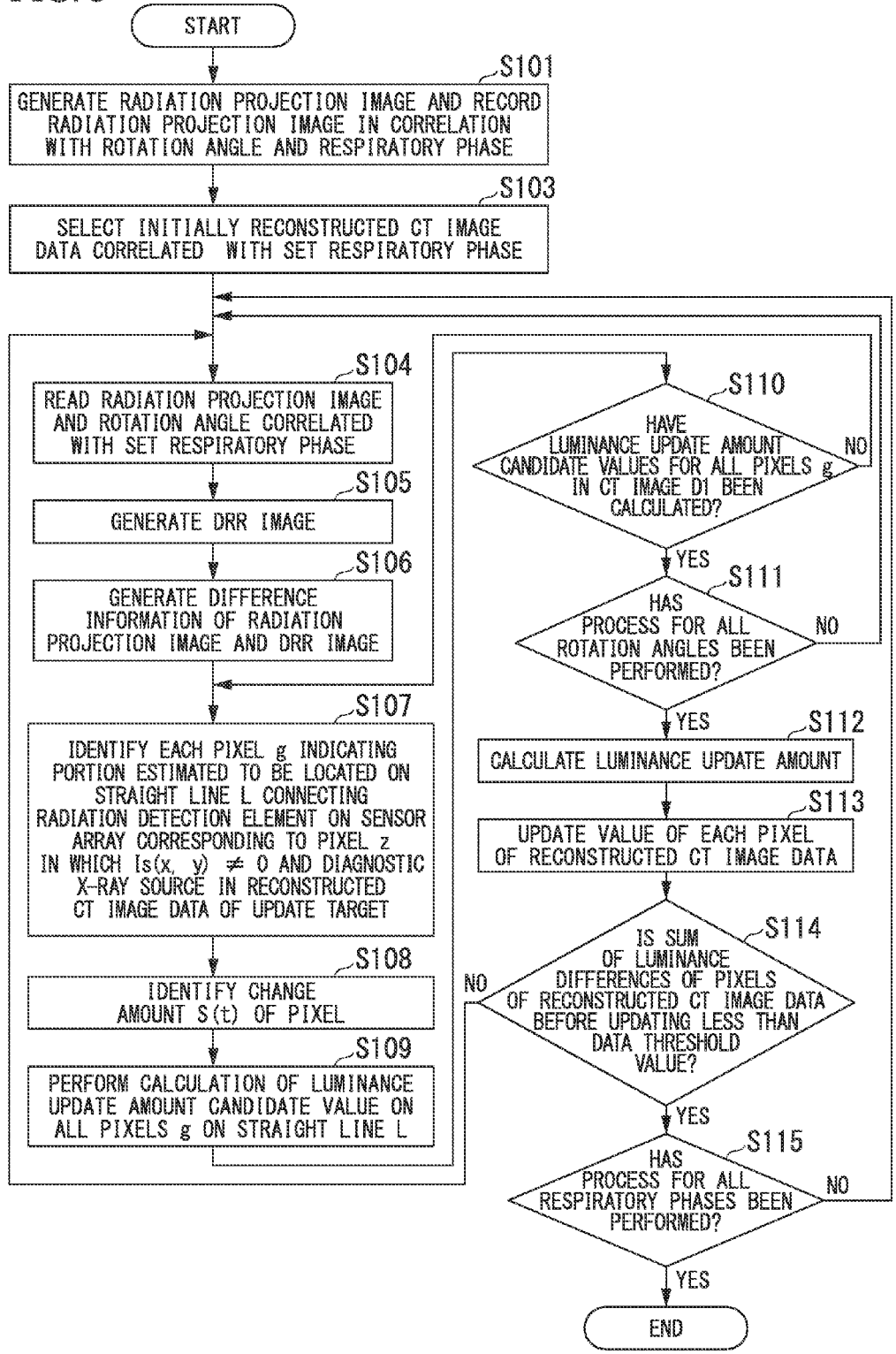
FIG. 3 is a diagram illustrating a process flow of the radiation therapy device controller.

FIG. 3 is a diagram illustrating a process flow of the radiation therapy device controller.

The control unit 101 instructs the radiation therapy device 3 to capture a radiation projection image including a diseased portion position. Then, the diagnostic X-ray source 24 irradiates the living body with radiation, and the radiation therapy device controller 1 receives a signal detected by the sensor array 32 or position data of the infrared marker acquired by an infrared sensor, which is not shown. As described above, a period and phase of a periodic motion of the infrared marker correspond to a respiratory period and phase.

Also, the radiation projection image generation unit 103 generates a radiation projection image including the diseased portion position of the living body corresponding to a first rotation angle of rotation angles An (n=1 . . . n). The radiation projection image generation unit 103 records, in the database 111, the generated radiation projection image in correlation with the rotation angle and the information relating to the respiratory phase extracted from the data of the phase acquired by the infrared sensor when the radiation is radiated (step S101).

While the reconstructed CT image data is created in a plurality of respiratory phases in the present process, a process in one respiratory phase (hereinafter referred to as a respiratory phase p1) will be hereinafter described.

The control unit 101 instructs the CT image selection unit 102 to start the process. The CT image selection unit 102 reads the set respiratory phase p1 from a memory. Also, the CT image selection unit 102 selects CT image data $_sD1'$ recorded in correlation with a respiratory phase p1' closest to the set respiratory phase p1 from the initially set CT image data group recorded in the database 111, and uses the CT image data $_sD1'$ as initial reconstructed CT image data $_kD1$ (step S103). The CT image selection unit 102 then reads the radiation projection image and the rotation angle (rotation angle A1) recorded in correlation with the respiratory phase p1 among combination data of (the radiation projection image, the rotation angle, and the respiratory phase) recorded in the database 111 (step S104).

Figure 4:
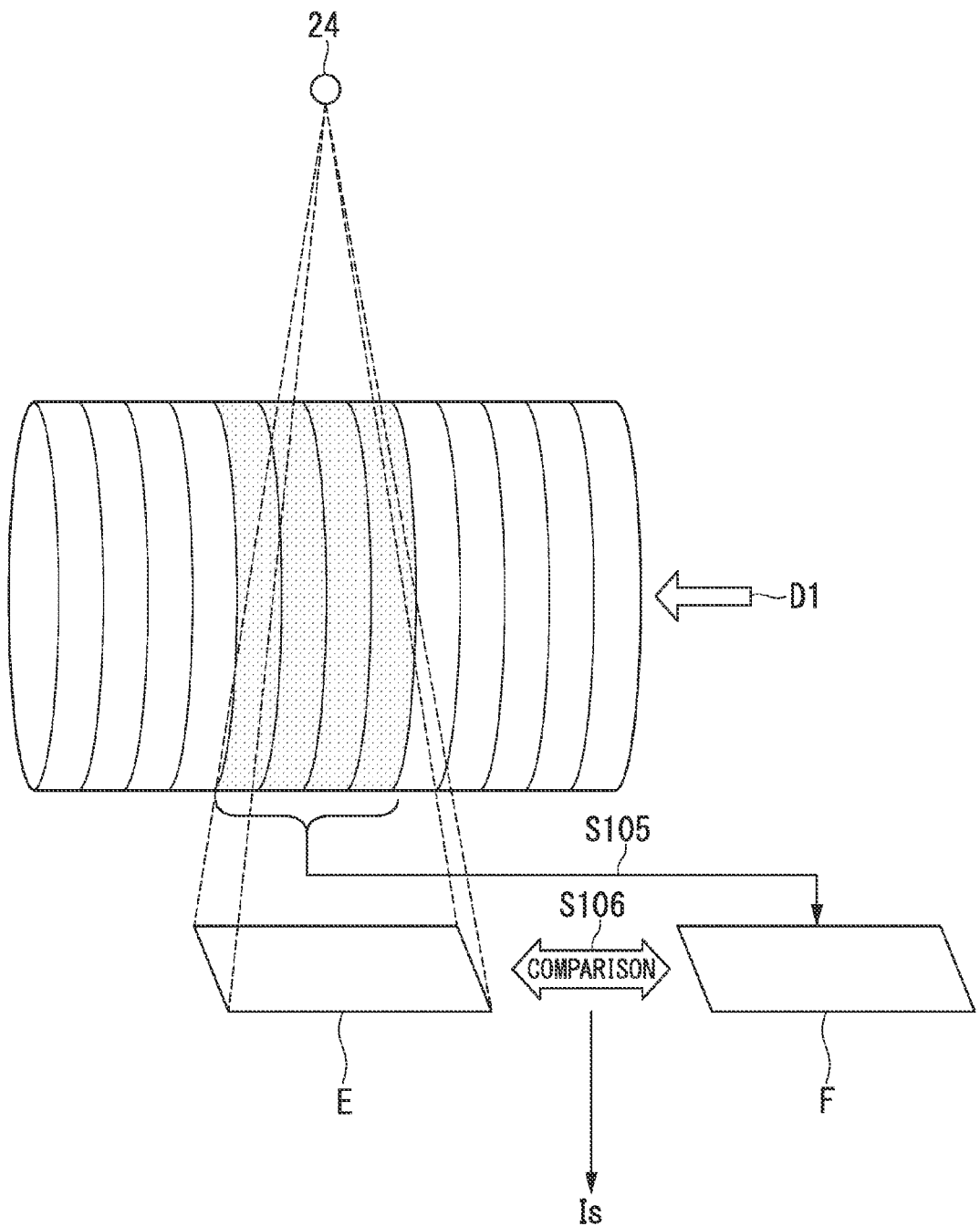
FIG. 4 is a diagram illustrating an overview of a difference information generation process.

FIG. 4 is a diagram illustrating an overview of a difference information generation process.

Initially set CT image data shown in FIG. 4 represents CT image data D1 (the reconstructed CT image data $_kD1$ when the initially set CT image data $_sD1$ has been updated) recorded in correlation with the one respiratory phase p1 among the CT image data included in the initially set CT image data group. Further, a radiation projection image E is a radiation projection image generated when the living body has been photographed at a rotation angle A1 in the respiratory phase p1. Hereinafter, the radiation projection image E is described as a radiation projection image (respiratory phase p1, rotation angle A1).

Next, the reconstructed image generation unit 106 generates a reconstructed image using the reconstructed CT image data (the initially set CT image data selected by the CT image selection unit 102 when a first updating process is performed) (step S105). In this case, if the rotation angle is A1, the reconstructed image generation unit 106 generates the reconstructed image when the radiation from the diagnostic X-ray source 24 is assumed to be projected to a living body shown by the CT image.

A generation overview of the reconstructed image is shown in FIG. 4. The reconstructed image indicates, for example, a DRR (Digital Reconstructed Radiography) image. Hereinafter, the reconstructed image will be referred to as a DRR image F.

Further, the DRR image F generated in step S105 is described as a DRR image (respiratory phase p1, rotation angle A1). A method of generating the DRR image F is known technology. Also, when the DRR image (respiratory phase p1, rotation angle A1) is generated, the difference information generation unit 107 compares pixels of the radiation projection image (respiratory phase p1, rotation angle A1) with pixels of the generated DRR image (respiratory phase p1, rotation angle A1), and generates difference information indicating a luminance difference for the pixels (difference information in the case of the respiratory phase p1 and the rotation angle A1) (step S106).

More specifically, when a luminance value of the radiation projection image (respiratory phase p1, rotation angle A1) is Ik(x, y) and a luminance value of the DRR image is Id(x, y) (x and y indicate a position indicated by an x coordinate and a y coordinate from an origin of a pixel of each image), the difference information Is(x, y) can be represented by:

$$Is(x,y)=Id(x,y)-Ik(x,y).$$

That is, the difference information is information indicating a difference between the luminance values of pixels of the radiation projection image (respiratory phase p1, rotation angle A1) and the DRR image (respiratory phase p1, rotation angle A1). Here, if Is(x, y)≠0, it shows that there is a difference between information in a real living body from which the radiation projection image (respiratory phase p1, rotation angle A1) is generated and the reconstructed CT image data from which a DRR image (respiratory phase p1, rotation angle A1) is generated on the straight line L connecting the radiation detection element of the sensor array 32 corresponding to the pixel indicated by the coordinate (x, y) and the diagnostic X-ray source 24. Also, when the difference information generation unit 107 generates the difference information, the difference information generation unit 107 registers the difference information (respiratory phase p1, rotation angle A1) in the database 111.

When the difference information (respiratory phase p1, rotation angle A1) is generated, the control unit 101 instructs the luminance update amount calculation unit 108 to start a process. In this case, the luminance update amount calculation unit 108 reads the reconstructed CT image data $_kD1$ of an update target (which is used to create the DRR image among the CT images). Further, the luminance update amount calculation unit 108 reads the difference information (respiratory phase p1, rotation angle A1) and identifies a pixel z in which Is(x, y)≠0 in the difference information (respiratory phase p1, rotation angle A1). Next, the luminance update amount calculation unit 108 identifies each pixel g indicating a portion estimated to be located on a straight line L connecting the radiation detection element on the sensor array 32 corresponding to the pixel z and the diagnostic X-ray source 24 in the reconstructed CT image data $_kD1$ of the update target (which is used to create the DRR image among the CT images) (step S107). Further, the luminance update amount calculation unit 108 reads the initially set CT image data $_sD1'$ of the respiratory phase p1' (the respiratory phase closest to the respiratory phase p1 in the initially set CT image data group described above) from the database 111. The luminance update amount calculation unit 108 also reads initially set CT image data $_sD2'$ that is at a closest phase p2' in a range of values smaller than the respiratory phase p1' indicated by the identified reconstructed CT image data D1 of an update target, from the database 111. Further, the luminance update amount calculation unit 108 reads initially set CT image data $_sD3'$ that is at a closest phase p3' in a range of values greater than the respiratory phase p1' indicated by the CT image data D1 of the update target, from the database 111. As described above, the phases p2' and p3' are the closest phases in the range greater or smaller than the phase p1'. Therefore, $_sD2'$, $_sD1'$, and $_sD3'$ of the CT image are initially set CT images corresponding to three successive respiratory phases in the initially set CT image data group.

Figure 5:
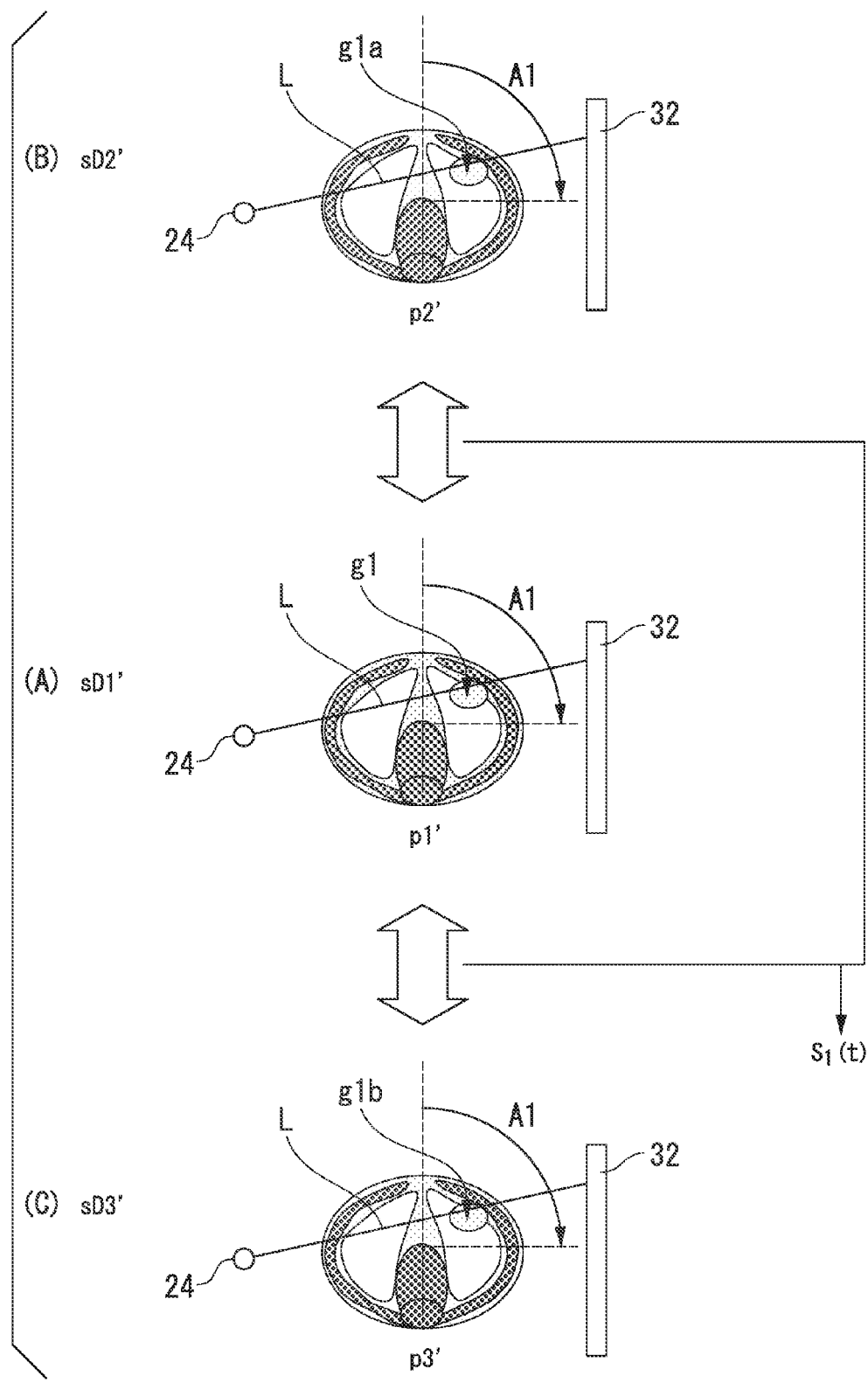
FIG. 5 is a diagram illustrating an overview of a process of calculating a change amount $S_1(t)$ of a pixel.

FIG. 5 is a diagram illustrating an overview of a process of calculating a change amount $S_1(t)$ of the pixel.

The luminance update amount calculation unit 108 calculates an absolute value d1 of a luminance difference between one pixel g1 among the pixels g of the identified initially set CT image data $_sD1'$ (respiratory phase p1') and a pixel g1a corresponding to the pixel g1 in the initially set CT image data $_sD2'$ (respiratory phase p2'), as shown in (A) and (B) of FIG. 5.

Further, the luminance update amount calculation unit 108 calculates an absolute value d2 of a luminance difference between the one pixel g1 of the initially set CT image data $_sD1'$ (respiratory phase p1') and a pixel g1b corresponding to the pixel g1 in the initially set CT image data $_sD3'$ (respiratory phase p3'), as shown in (A) and (C) of FIG. 5. Further, the luminance update amount calculation unit 108 identifies a greater value of the absolute value d1 and the absolute value d2 as the change amount $S_1(t)$ of the pixel g1 (step S108).

Here, a straight line L is L(t)=(Lx(t), Ly(t), Lz(t)), and t is defined as 0<t<1.

Further, the luminance value of the pixel g1 of the initially set CT image data $_sD1'$ (respiratory phase p1') is D1'(Lx(t), Ly(t), Lz(t)).

Similarly, the luminance value of the pixel g1a of the initially set CT image data $_sD2'$ (respiratory phase p2') is D2'(Lx(t), Ly(t), Lz(t)).

Similarly, the luminance value of the pixel g1b of the initially set CT image data $_sD3'$ (respiratory phase p3') is D3'(Lx(t), Ly(t), Lz(t)).

Then, the change amount $S_1(t)$ can be represented by the following formula (1). Here, "max" is a function taking a maximum value of an argument, and "abs" is a function taking an absolute value of an argument. $S_1(t)$ represents a degree of easiness of change in luminance value of the pixel in the reconstructed CT image data. Here, a change amount of the luminance when the respiratory phase is changed is regarded as the degree of easiness of change in luminance.

[Formula 1]

$$S_1(t)=\max[\text{abs}\{D2'(Lx(t),Ly(t),Lz(t))-D1'(Lx(t),Ly(t),Lz(t))\},\text{abs}\{D3'(Lx(t),Ly(t),Lz(t))-D1'(Lx(t),Ly(t),Lz(t))\}] \quad (1)$$

This is a process of calculating a first change amount $S_1(t)$. Also, the luminance update amount calculation unit 108 performs the same calculation process in a plurality of pixels g identified as those indicating a portion estimated to be located on a straight line L connecting the radiation detection element on the sensor array 32 corresponding to the pixel z and the diagnostic X-ray source 24. Further, in order to improve resolution, it is desirable for this calculation process to be performed on all pixels. Hereinafter, the same calculation process is assumed to be performed in all the pixels.

In the above description, both the respiratory phase p2' and the respiratory phase p3' are used, but only one of the respiratory phases may be used.

In addition, the luminance update amount calculation unit 108 may calculate a change amount S(t) using a process of calculating a second change amount $S_2(t)$ or a process of calculating a third change amount $S_3(t)$, which will be described below, instead of the process of calculating a first change amount $S_1(t)$.

(Process of Calculating a Second Change Amount $S_2(t)$)

In the process of calculating a second change amount $S_2(t)$, the luminance update amount calculation unit 108 reads the difference information and identifies a pixel in which Is(x, y)≠0 in the difference information. Also, the luminance update amount calculation unit 108 identifies each pixel g1 corresponding to a portion estimated to be located on a straight line L connecting the radiation detection element on the sensor array 32 corresponding to the pixel and the diagnostic X-ray source 24, in the reconstructed CT image data $_kD1$ of an update target (which is used to create the DRR image among the CT images). The process up to this point is the same as the process of calculating a first change amount $S_1(t)$. Further, the luminance update amount calculation unit 108 reads initially set CT image data sD1' of the respiratory phase p1' from the database 111. Further, the luminance update amount calculation unit 108 reads a plurality of radiation projection images, including a radiation projection image generated at a rotation angle at which the respiratory phase differs from p1, from the database 111. Also, the luminance update amount calculation unit 108 generates CT image data D4 using the plurality of radiation projection images at the different rotation angles. The process of generating the CT image using the plurality of radiation projection images at the different rotation angles is known technology.

Also, the luminance update amount calculation unit 108 identifies an absolute value of a luminance difference between a pixel g1 of the identified initially set CT image data sD1' (respiratory phase p1') and a pixel g1c corresponding to the pixel g1 in the CT image D4 generated using the plurality of radiation projection images with the different rotation angles, as a change amount S(t) of the pixel g1. Also, if the luminance value of the pixel g1 of the initially set CT image data $_sD1'$ (respiratory phase p1') is D1'(Lx(t), Ly(t), Lz(t)) and the luminance value of the pixel g1c of the CT image D4 is D4(Lx(t), Ly(t), Lz(t)), the change amount $S_2(t)$ can be calculated by the following formula (2):

[Formula 2]

$$S_2(t)=\text{abs}\{D4(Lx(t),Ly(t),Lz(t))-D1'(Lx(t),Ly(t),Lz(t))\} \quad (2)$$

(Process of Calculating a Third Change Amount $S_3(t)$)

The process of calculating a first change amount $S_1(t)$ and the process of calculating a second change amount $S_2(t)$ are first performed in the process of calculating a third change amount $S_3(t)$. Also, using results of the process of calculating a first change amount $S_1(t)$ and the process of calculating a second change amount $S_2(t)$, the change amount $S_3(t)$ of the pixel g1 is calculated by a formula:

$$S_3(t)=\alpha S_1(t)+\beta S_2(t).$$

α and β are coefficients. For example, calculation in which α=0.5 and β=0.5 is performed.

Figure 6:
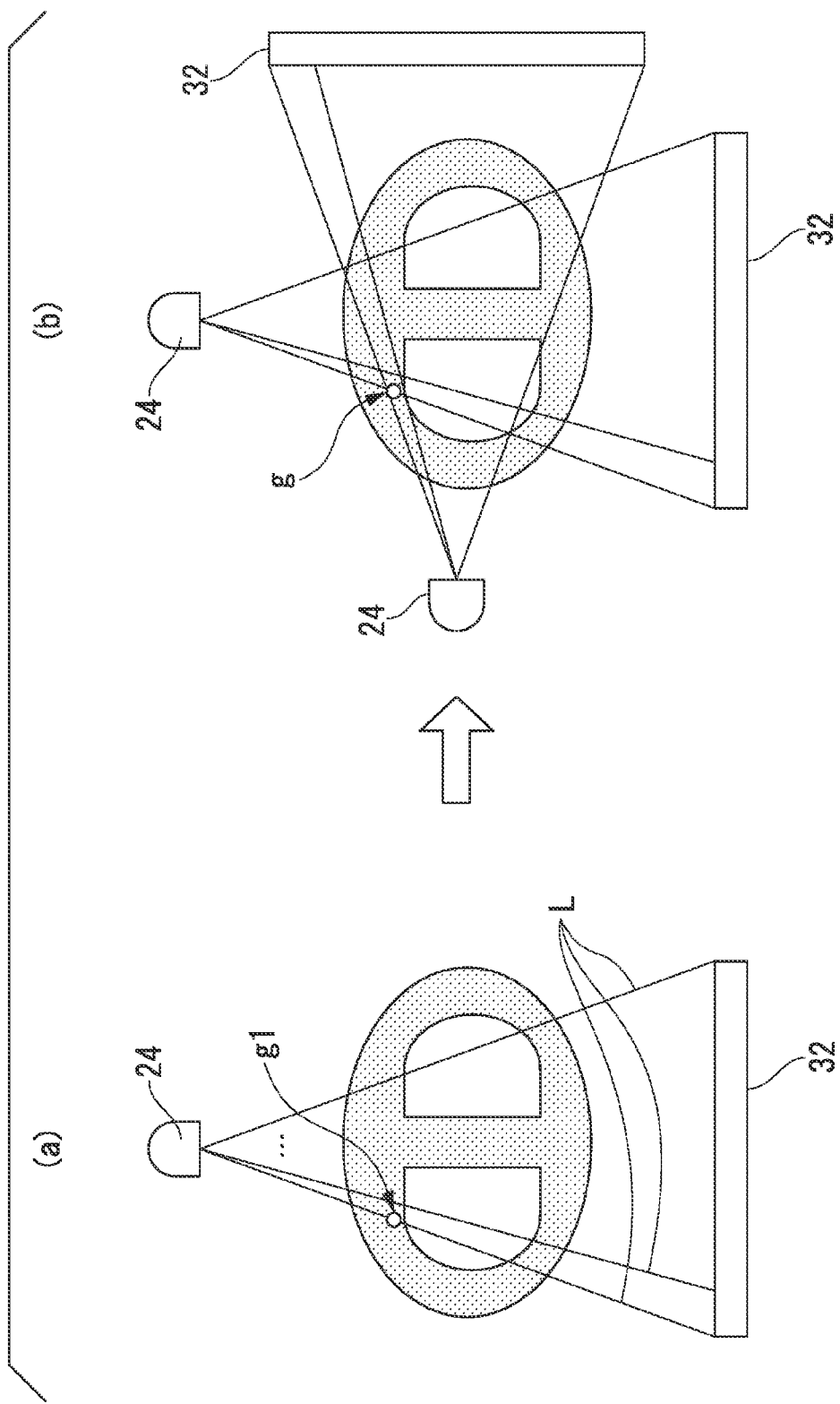
FIG. 6 is a diagram illustrating an overview of a process of calculating a luminance update amount.

FIG. 6 is a diagram illustrating an overview of a process of calculating a luminance update amount.

As shown in FIG. 6(a), if the process of calculating any one of the first to third change amounts S(t) is finished, the luminance update amount calculation unit 108 calculates a sum (ΣS(t)) of change amounts S(t) calculated for all the pixels g. Further, the luminance update amount calculation unit 108 calculates a ratio (S(t)÷ΣS(t)) of the change amount S(t) calculated for one pixel g1 corresponding to a certain portion on the straight line L to the sum of change amounts S(t). Also, the luminance update amount calculation unit 108 multiplies the ratio of S(t) by the luminance difference Is indicated by the difference information calculated for the pixel z. In this way, the luminance update amount calculation unit 108 calculates a luminance update amount candidate value that is a value obtained by distributing information of a difference represented by the luminance difference calculated for the pixel z to one pixel g1 corresponding to a portion estimated to be on the straight line L of the CT image data D1. This luminance update amount candidate value is R(x, y, z). This process is performed on all the pixels g on the straight line L (step S109).

If the processing of the luminance update amount candidate value is finished, the luminance update amount calculation unit 108 determines whether the luminance update amount candidate value has been calculated for all radiation detection elements (pixels) on the sensor array 32 (step S110), and repeats the process of steps S107 to S109 described above if the luminance update amount candidate value has not been calculated.

When the answer is "yes" in step S110, the control unit 101 determines whether the process has been performed on all rotation angles recorded in the database 111 in correlation with the respiratory phase p1 that is a target (step S111). If the process has not been performed on all the rotation angles recorded in the database 111 in correlation with the respiratory phase p1 that is a target, the control unit 101 changes the rotation angle A1, sets a next rotation angle A2, instructs to start the process of steps S103 to S110 described above using the radiation projection image of the rotation angle A2, and repeats the process up to the rotation angle An. Through the above process, a plurality of pieces of difference information of the respiratory phase p1 and the rotation angles A1 to An, and the luminance update amount candidate value R(x, y, z) of the pixel in the reconstructed CT image data $_kD1$ of each combination of the respiratory phase p1 and the rotation angles A1 to An are recorded in the database 111.

Next, the luminance update amount calculation unit 108 calculates the luminance update amount of each pixel whose luminance update amount candidate value has been calculated, in the reconstructed CT image data $_kD1$, using the luminance update amount candidate value for each pixel in the reconstructed CT image data $_kD1$ calculated for each of the rotation angles A1 to An for the respiratory phase p1 (step S112).

More specifically, as shown in (b) of FIG. 6, the luminance update amount calculation unit 108 calculates an average of the luminance update amount candidate value R(x, y, z) calculated for each of the rotation angles A1 to An for a pixel in the reconstructed CT image data $_kD1$ of the respiratory phase p1, as the luminance update amount.

Alternatively, if the radiation projection image generated in step S101 for each repeated process at the rotation angles A1 to An based on the determination of step S111 is generated at a timing of a different respiratory phase, the luminance update amount calculation unit 108 may calculate the luminance update amount by performing weighting in such a manner that a weight of the luminance update amount candidate value R(x, y, z) when the process of steps S102 to S109 is performed using the radiation projection image generated at a timing of the respiratory phase closest to the respiratory phase indicated by the reconstructed CT image data $_kD1$ is greatest. For example, if the respiratory phase indicated by the reconstructed CT image data $_kD1$ is p and the luminance update amount candidate value calculated using the radiation projection image in which the rotation angle is Ai and the respiratory phase is pi is Ri, the luminance update amount D of the pixel g(x, y, z) whose luminance update amount candidate value in the reconstructed CT image data $_kD1$ has been calculated is calculated by:

[Formula 3]

$$D(x,y,z)=\Sigma\{(\omega i \cdot Ri)\div\Omega\} \quad (3)$$

Here, Ω in Formula (3) shows Ω=Σωi. For example, ωi is

[Formula 4]

$$\omega i=1\div(abs(p-pi)+1) \quad (4)$$

The CT image updating unit 109 adds the luminance update amount D calculated for each pixel whose luminance update amount candidate value in the reconstructed CT image data $_kD1$ has been calculated to a value of the corresponding pixel in the reconstructed CT image data $_kD1$ of the respiratory phase p1 that is a target to update the value of each pixel of the reconstructed CT image data $_kD1$ and update the reconstructed CT image data into the reconstructed CT image data $_{k+1}D1$ (step S113). Next, the control unit 101 compares the reconstructed CT image data $_{k+1}D1$ after the updating process with the reconstructed CT image data $_kD1$ before the updating process. In this comparison process, a luminance difference between a certain pixel of the reconstructed CT image data $_{k+1}D1$ after the updating process and the pixel of the reconstructed CT image data $_kD1$ before the updating corresponding to the certain pixel is calculated for all corresponding pixels, and it is determined whether a sum thereof is less than a threshold value (step S114). Also, if the sum is less than the threshold value, it is determined that the process ends using the reconstructed CT image data D1 after the updating process. If the sum is greater than or equal to the threshold, the process from step S104 is repeated ($_k$ of $_kD1$ is updated to $_{k+1}D1$). In the repeated process, the reconstructed CT image data ($_{k+1}D1$) after the updating process is used.

Further, if the sum is less than the threshold in step S114, it is determined whether the process of steps S102 to S114 has been performed on all respiratory phases pm (m=1 ... m) that are reconstructed CT image data creation targets (step S115). If the process has not been performed, the process of the steps S101 to S114 is performed on other respiratory phases. Accordingly, the process of updating the CT images for all the respiratory phases pm is finished.

Here, according to the process of updating the CT image described above, the process of updating the data is performed using the CT image data group (initially set CT image data group) created in advance and recorded in the database 111. Accordingly, if the CT image data group already recorded in the database 111 directly before the radiation is radiated to the diseased portion is used, it is possible to obtain a high-quality CT image in a short time by performing only the above-described updating process using the newly generated radiation projection image. Also, it is possible to irradiate a diseased portion position with the radiation with high accuracy by performing the process of tracking the diseased portion using the high-quality CT image.

Further, according to the process described above, since the luminance update amount only for each pixel whose luminance update amount candidate value has been calculated and the process of updating the CT image is performed using the luminance update amount, it is not necessary to perform the updating process on the pixel whose luminance update amount candidate value has not been calculated. Accordingly, it is possible to shorten a time to complete the updating process by pixels on which the updating process is not performed.

Figure 7:
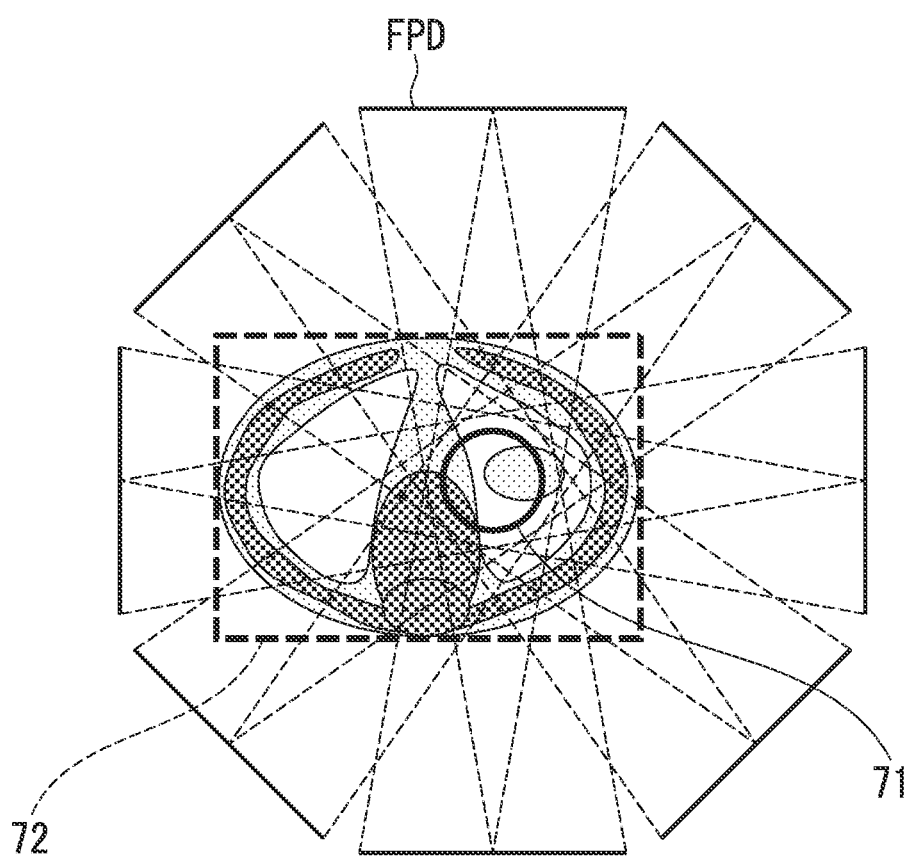
FIG. 7 is a diagram illustrating a difference with a range of a CT image in which a conventional updating process can be performed.

FIG. 7 is a diagram illustrating a difference with a range of a CT image on which a conventional updating process can be performed.

In a method of creating a CT image in conventional technology using an FBP method, a circular range 71 of a CT image that can be generated by a plurality of radiation projection images is a target. Further, a dashed line in FIG. 7 indicates a range that can be photographed in each sensor array (FPD). In the process of updating a high-quality CT image according to the present embodiment, since the CT image generated in advance can be selected by a user and the updating process can be performed on the entire CT image, it is possible to perform the process of updating a CT image (a rectangular CT image range 72) whose range is wider than that of the related art (creation of a high-quality CT image).

Also, the radiation therapy device controller 1 performs the process of tracking the diseased portion using the CT image after the updating process described above, and performs radiation radiating control on the tracked diseased portion. Here, the diseased portion position tracking unit 110 of the radiation therapy device controller 1 inputs the information of the respiratory phase over time of the living body indicated by the infrared marker, from the radiation therapy device 3 that has detected the motion of the infrared marker attached to the living body using the infrared camera. Further, the diseased portion position tracking unit 110 displays the CT image of each respiratory phase after the updating process on a display unit (e.g., a monitor) connected to the radiation therapy device controller 1, based on a manipulation of the user. Also, the user selects the diseased portion position in the CT image after the updating process of each respiratory phase, and the control unit 101 receives information of the diseased portion position. For example, the control unit 101 receives a designation of a coordinate of the diseased portion position in the CT image for each respiratory phase as the diseased portion information. Based on the coordinate (movement phase) of the diseased portion position in the CT image for each respiratory phase, and the respiratory phase over time based on the motion of the infrared marker, the diseased portion position tracking unit 110 generates a correlation model formula between the respiratory phase and the movement phase of the diseased portion. Also, the diseased portion position tracking unit 110 registers the generated correlation model formula in the database 111.

In the tracking process, the diseased portion position tracking unit 110 of the radiation therapy device controller 1 acquires the information of the respiratory phase over time indicated by the infrared marker attached to the living body from the radiation therapy device 3 and calculates the diseased portion position corresponding to the respiratory phase over time using the correlation model formula over time. Also, the diseased portion position tracking unit 110 sequentially transmits the calculated diseased portion position to the radiation therapy device 3 over time and the radiation therapy device 3 radiates the received diseased portion position with radiation.

Through the process described above, it is possible to irradiate the diseased portion position with radiation with high accuracy by performing the tracking of the diseased portion position using the high-quality CT image after the updating process.

In the above embodiment, the radiation projection image has been shown by the example in which the radiation projection image is created based on the ray source and the sensor array included in the radiation therapy device. However, the radiation projection image may be created, for example, by a diagnostic device (a CT or an MRI) included separately from the radiation therapy device.

Further, the radiation therapy device controller or the radiation therapy device described above includes a computer system therein. Also, the process of each processing described above is stored in a computer-readable recording medium in the form of a program. As this program is read and executed by the computer, the processing is performed. Here, the computer-readable recording medium refers to a magnetic disk, a magneto-optical disc, a CD-ROM, a DVD-ROM, a semiconductor memory, or the like. Further, this computer program may be distributed to a computer through a communication line, and the computer receiving this distribution may execute the program.

Further, the above program may be a program for realizing some of the above-described functions.

Further, the program may be a program that can realize the above-described functions in combination with a program already recorded in the computer system, i.e., may be a so-called differential file (differential program).

INDUSTRIAL APPLICABILITY

Since the process of updating data is performed using the CT image data group (the initially set CT image data group) recorded in the database, it is possible to obtain a high-quality CT image in a short time by performing only the updating process using the newly generated radiation projection image.

DESCRIPTION OF REFERENCE NUMERALS

1 . . . radiation therapy device controller
3 . . . radiation therapy device
101 . . . control unit
102 . . . CT image selection unit
103 . . . radiation projection image generation unit
105 . . . rotation angle detection unit
106 . . . reconstructed image generation unit
107 . . . difference information generation unit
108 . . . luminance update amount calculation unit
109 . . . CT image updating unit
110 . . . diseased portion position tracking unit
111 . . . database

The invention claimed is:

1. A radiation therapy device controller including a computer system configured to control a radiation therapy device that irradiates a living body arranged between a ray source and a sensor array with radiation from the ray source to treat a diseased portion of the living body, the computer system including a computer, the controller comprising:

a computed tomography image selection unit, being performed by said computer, that selects, as computed tomography image data of an update target, the computed tomography image data of a set body motion phase from a computed tomography image data group generated for each body motion phase in advance;

a radiation projection image generation unit that rotates the ray source and the sensor array to generate a radiation projection image corresponding to each of a plurality of rotation angles, and records the radiation projection image, the rotation angle when rotating the ray source and the sensor array at the time of generating the radiation projection image, and a body motion phase at the time of generating the radiation projection image to be correlated with each other;

a rotation angle detection unit, being performed by said computer, that detects the rotation angle at the time of generating the radiation projection image;

a reconstructed image generation unit, being performed by said computer, that generates a reconstructed image when the computed tomography image data of the update target is projected from the ray source to the sensor array at the detected rotation angle;

a difference information generation unit, being performed by said computer, that compares each pixel of the radiation projection image with each pixel of the generated reconstructed image to generate difference information indicating a luminance difference for the each pixels;

a luminance update amount calculation unit, being performed by said computer, that identifies a pixel on a straight line connecting the ray source and a detection element of the sensor array in the computed tomography image data of the update target, calculates a luminance update amount candidate value for each identified pixel based on a degree of easiness of change in the luminance value of the identified pixel and the difference information, and calculates a luminance update amount of each identified pixel using the luminance update amount candidate value of each identified pixel calculated for a plurality of rotation angles corresponding to the body motion phase that is a target; and an updating unit, being performed by said computer, that updates a luminance value of each corresponding pixel of the computed tomography image data of the update target, using the luminance update amount of each identified pixel, wherein the computed tomography image is generated based on information detected by the sensor array.

2. The radiation therapy device controller according to claim 1, wherein the initially set computed tomography image and an image of a range in which the updating unit performs updating are a computed tomography image in a range wider than a range of a computed tomography image generated based on radiation projection images of a plurality of rotation angles.

3. The radiation therapy device controller according to claim 2, wherein the luminance update amount calculation unit obtains the degree of easiness of change in the luminance value based on a difference between an initially set computed tomography image of a body motion phase close to the body motion phase of the computed tomography image data of the update target and an initially set computed tomography image of another body motion phase close to the body motion phase of the initially set computed tomography image.

4. The radiation therapy device controller according to claim 2, wherein the luminance update amount calculation unit obtains the degree of easiness of change in the luminance value based on a difference between an initially set computed tomography image of a body motion phase close to the body motion phase of the computed tomography image data of the update target and the computed tomography image data of the update target generated based on the radiation projection image corresponding to an arbitrary body motion phase.

5. The radiation therapy device controller according to claim 4, the control device further comprising:

a diseased portion position tracking unit, being performed by said computer, that calculates a position of the diseased portion corresponding to a measured body motion phase of the living body to track the diseased portion position using a correlation model formula showing a correlation between the body motion phase of the living body and the position of the diseased portion in the living body.

6. A processing method, performed by a computer, for a radiation therapy device controller configured to control a radiation therapy device that irradiates a living body arranged between a ray source and a sensor array with radiation from the ray source to treat a diseased portion of the living body, the processing method comprising:

selecting, by said computer, as computed tomography image data of an update target, the computed tomography image data of a set body motion phase from a computed tomography image data group generated for each body motion phase in advance;

rotating the ray source and the sensor array to generate a radiation projection image corresponding to each of a plurality of rotation angles, and correlating, by said computer, the rotation angle with a separately acquired respiratory phase;

detecting, by said computer, the rotation angle at the time of generating the radiation projection image;

generating, by said computer, a reconstructed image when the computed tomography image data of the update target is projected from the ray source to the sensor array at the detected rotation angle;

comparing, by said computer, each pixel of the identified radiation projection image with each pixel of the generated reconstructed image to generate difference information indicating a luminance difference for the pixels;

identifying, by said computer, in the computed tomography image data of the update target, a pixel on a straight line connecting the ray source and the sensor array, calculating a luminance update amount candidate value for each identified pixel based on a degree of easiness of change in the luminance value of the identified pixel and the difference information, and calculating a luminance update amount of each identified pixel using the luminance update amount candidate value of each identified pixel calculated for a plurality of rotation angles corresponding to the body motion phase that is a target; and updating, by said computer, a luminance value of each corresponding pixel of the computed tomography image data of the update target, using the luminance update amount of each identified pixel, wherein the computed tomography image is generated based on information detected by the sensor array.

7. A non-transitory computer readable medium comprising a program for causing a computer of a radiation therapy device controller for controlling a radiation therapy device that irradiates a living body arranged between a ray source and a sensor array with radiation from the ray source to treat a diseased portion of the living body, to function as:

a computed tomography image selection device that selects, as computed tomography image data of an update target, the computed tomography image data of a set body motion phase from a computed tomography image data group generated for each body motion phase in advance;

a radiation projection image generation device that rotates the ray source and the sensor array to generate a radiation projection image corresponding to each of a plurality of rotation angles, and correlates the rotation angle with a separately acquired respiratory phase;

a rotation angle detection device that detects the rotation angle at the time of generating the radiation projection image;

a reconstructed image generation device that generates a reconstructed image when the computed tomography image data of the update target is projected from the ray source to the sensor array at the detected rotation angle;

a difference information generation device that compares each pixel of the radiation projection image with each pixel of the generated reconstructed image to generate difference information indicating a luminance difference for the pixels;

a luminance update amount calculation device that identifies, in the computed tomography image data of the update target, a pixel on a straight line connecting the ray source and the sensor array, calculates a luminance update amount candidate value for each identified pixel based on a degree of easiness of change in the luminance value of the identified pixel and the difference information, and calculates a luminance update amount of each identified pixel using the luminance update amount candidate value of each identified pixel calculated for a plurality of rotation angles corresponding to the body motion phase that is a target; and an updating device that updates a luminance value of each corresponding pixel of the computed tomography image data of the update target, using the luminance update amount of each identified pixel, wherein the computed tomography image is generated based on information detected by the sensor array.

* * * * *